US009783477B2

(12) United States Patent
Sutton et al.

(10) Patent No.: US 9,783,477 B2
(45) Date of Patent: Oct. 10, 2017

(54) SYNTHESIS OF FUELS AND FEEDSTOCKS

(71) Applicant: Los Alamos National Security, LLC, Los Alamos, NM (US)

(72) Inventors: Andrew D. Sutton, Los Alamos, NM (US); Ty Brooks, Los Alamos, NM (US); Rhodri Jenkins, Los Alamos, NM (US); Cameron Moore, Los Alamos, NM (US); Orion Staples, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 15/205,982

(22) Filed: Jul. 8, 2016

(65) Prior Publication Data

US 2017/0029351 A1  Feb. 2, 2017

Related U.S. Application Data

(60) Provisional application No. 62/199,669, filed on Jul. 31, 2015.

(51) Int. Cl.
| | | |
|---|---|---|
| C07C 45/62 | (2006.01) | |
| C07C 45/72 | (2006.01) | |
| C07C 45/00 | (2006.01) | |
| C07C 29/145 | (2006.01) | |
| C01B 3/22 | (2006.01) | |
| C07C 1/22 | (2006.01) | |

(52) U.S. Cl.
CPC ............ *C07C 45/72* (2013.01); *C01B 3/22* (2013.01); *C07C 1/22* (2013.01); *C07C 29/145* (2013.01); *C07C 45/002* (2013.01); *C07C 45/62* (2013.01); *C01B 2203/0277* (2013.01); *C01B 2203/06* (2013.01); *C01B 2203/1041* (2013.01); *C01B 2203/1229* (2013.01); *C07C 2521/18* (2013.01); *C07C 2523/44* (2013.01); *C07C 2531/10* (2013.01)

(58) Field of Classification Search
CPC ............ C07C 45/72; C07C 45/62; C01B 3/22

USPC .......................................................... 568/396
See application file for complete search history.

(56) References Cited

U.S. PATENT DOCUMENTS

| | | | | |
|---|---|---|---|---|
| 3,946,085 A | * | 3/1976 | Adolph .................. | C06B 43/00 149/88 |
| 5,583,263 A | * | 12/1996 | Muthusamy ............ | C07C 45/62 568/390 |
| 6,803,487 B2 | * | 10/2004 | Ebner .................... | C07C 17/275 568/449 |
| 2016/0008801 A9 | * | 1/2016 | Yamaguchi ........... | C07C 45/002 423/658.2 |

FOREIGN PATENT DOCUMENTS

WO  WO 2013/040311  3/2013

OTHER PUBLICATIONS

Sutton, et al., "The hydrodeoxygenation of bioderived furans into alkanes," *Nature Chemistry*, 5:428-432, Apr. 7, 2013.
Sutton et al., "Adding Value to Biomass—Green Gold!" Gordon Research Conference—Inorganic Reaction Mechanisms Poster, Mar. 2015.
Sutton, Andrew D., "Adding Value to Biomass—Green Gold!" Gordon Research Conference—Inorganic Reaction Mechanisms, slides for oral presentation—Mar. 3, 2015.

* cited by examiner

*Primary Examiner* — Sikarl Witherspoon
(74) *Attorney, Agent, or Firm* — Klarquist Sparkman, LLP

(57) ABSTRACT

Disclosed herein are embodiments of a method for making fuels and feedstocks from readily available alcohol starting materials. In some embodiments, the method concerns converting alcohols to carbonyl-containing compounds and then condensing such carbonyl-containing compounds together to form oligomerized species. These oligomerized species can then be reduced using by-products from the conversion of the alcohol. In some embodiments, the method further comprises converting saturated, oligomerized, carbonyl-containing compounds to aliphatic fuels.

18 Claims, 5 Drawing Sheets

SYNTHESIS OF FUELS AND FEEDSTOCKS

CROSS REFERENCE TO RELATED APPLICATION

This application claims the benefit of and priority to the earlier filing date of U.S. Provisional Patent Application No. 62/199,669, filed on Jul. 31, 2015, the entirety of which is incorporated by reference herein.

ACKNOWLEDGMENT OF GOVERNMENT SUPPORT

This invention was made with government support under Contract No. DE-AC52-06NA25396 awarded by the U.S. Department of Energy. The government has certain rights in the invention.

FIELD

The present disclosure concerns low temperature, catalytic methods of making fuels and feedstocks, such as aliphatic hydrocarbons, from readily available alcohol compounds.

BACKGROUND

Sustainable methods of making transportation fuels, such as hydrocarbon compounds, from renewable resources is becoming increasingly important. Methods of producing fuels from biomass-derived components have been explored, as have methods using other readily-available materials, such as carbohydrates, glycerol, dihydroxyacetone, and the like. Desirable fuels often comprise long hydrocarbon chains, therefore, it often is necessary to extend the carbon chain of the starting materials that are used. Conventional methods to obtain such fuels typically produce mixtures of products having varying chain lengths and therefore exhibit poor selectivity, which can be undesirable for certain applications. Such methods often require elevated temperatures and organic solvents, which can prevent the use of such methods in industrial applications. Other conventional methods require using expensive catalysts that are not capable of promoting reactions with particular compounds, thereby limiting their applicability. Additionally, conventional methods often rely on cellulosic materials or sugars as feedstocks for the reactions used to produce fuels.

There exists a need in the art for a method of producing fuels that utilizes readily available starting materials and feedstocks, low-cost, non-toxic reactants, and that are readily scaled so as to be useful in industry.

SUMMARY

Disclosed herein are embodiments of methods comprising: exposing an alcohol or mixture of alcohols to a dehydrogenation catalyst capable of dehydrogenating the alcohol or mixture of alcohols to produce a carbonyl-containing compound or a mixture of carbonyl-containing compounds, and $H_2$; exposing the carbonyl-containing compound or mixture of carbonyl-containing compounds to a solid acid catalyst to produce an oligomerized condensation product comprising an α,β-unsaturated carbonyl group; and exposing the condensation product to the $H_2$ produced from dehydrogenating the alcohol or mixture of alcohols to produce a saturated, oligomerized carbonyl-containing compound. In other embodiments, the method can comprise utilizing an aldehyde starting material to perform the condensation step. In some embodiments, the method further comprises exposing the saturated oligomerized carbonyl-containing compound to a metal catalyst, a solid acid catalyst, or a combination thereof, at a temperature below 200° C. to form an aliphatic compound. In additional embodiments, the method can further comprise adding an alcohol solvent to convert a carbonyl-containing compound comprising an α,β-unsaturated carbonyl group to an acetal-containing compound or adding an alcohol solvent to convert a saturated carbonyl-containing compound to a saturated acetal-containing compound. The dehydrogenation catalyst capable of dehydrogenating the alcohol or mixture of alcohols can comprise a non-precious metal selected from cobalt, manganese, or iron. The carbonyl-containing compound can have a formula

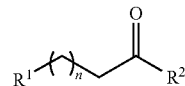

wherein each of $R^1$ and $R^2$ is hydrogen or aliphatic, typically alkanes or alkenes, and n ranges from 0 to 50.

In some embodiments, the condensation product is formed by a condensation reaction between two carbonyl-containing compounds having the same structure and wherein the condensation product has a structure satisfying a formula

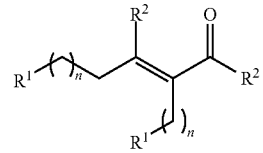

wherein each $R^1$ and $R^2$ is hydrogen or aliphatic, and each n ranges from 0 to 50.

In some embodiments, the condensation product is formed by a condensation reaction between a mixture of carbonyl-containing compounds having different structures and wherein the condensation product has a structure satisfying a formula

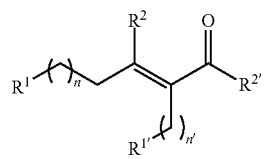

wherein each $R^1$, $R^{1'}$, $R^2$, and $R^{2'}$ independently is selected from hydrogen or aliphatic; and each of n and n' independently is selected from 0 to 50.

Exposing the carbonyl-containing compound or mixture of carbonyl-containing compounds to a solid acid catalyst can comprise reacting the carbonyl-containing compound or mixture of carbonyl-containing compounds with a styrene-divinylbenzene polymer acid or a sulfonated tetrafluoroethylene-based fluoropolymer-copolymer. In some embodiments, exposing the condensation product to the $H_2$ produced from dehydrogenating the alcohol or mixture of alcohols can comprise transferring $H_2$ from a first reaction vessel wherein the alcohol or mixture of alcohols has been dehydrogenated to a second reaction vessel comprising the condensation product. In yet other embodiments, exposing the condensation product to the $H_2$ produced from dehydrogenating the alcohol or mixture of alcohols can comprise adding the solid acid catalyst into a reaction vessel comprising the $H_2$ gas and the carbonyl-containing compound or the mixture of carbonyl-containing compounds.

In some embodiments, the method further comprises repeating steps of exposing the carbonyl-containing compound or mixture of carbonyl-containing compounds to a solid acid catalyst to obtain an oligomerized carbonyl-containing compound having a structure satisfying a formula

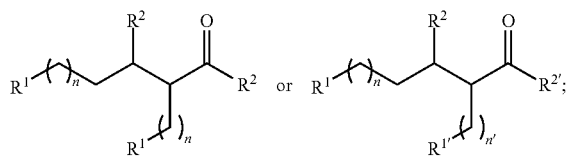

wherein each $R^1$, $R^{1'}$, $R^2$, and $R^{2'}$ independently is selected from hydrogen or aliphatic; each of n and n' independently is selected from 0 to 50; and each m independently is selected from 1-24.

Also disclosed herein are embodiments of a method of producing an aliphatic fuel compound, comprising exposing an alcohol or mixture of alcohols to a cobalt-, manganese-, or iron-containing dehydrogenation catalyst capable of dehydrogenating the alcohol or mixture of alcohols to produce $H_2$ and a carbonyl-containing compound having a structure satisfying a formula

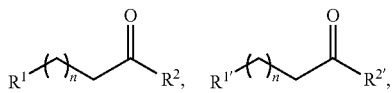

or a mixture thereof; exposing the carbonyl-containing compound or mixture thereof to a styrene-divinylbenzene polymer acid or a sulfonated tetrafluoroethylene-based fluoropolymer-copolymer to produce an unsaturated oligomerized condensation product having a structure satisfying a formula

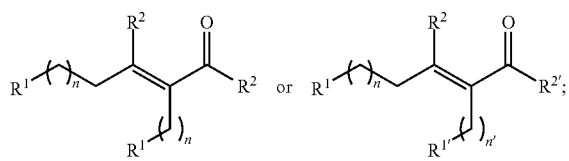

and exposing the oligomerized condensation product to the $H_2$ produced from dehydrogenating the alcohol or mixture of alcohols to produce a saturated oligomerized carbonyl-containing compound having a structure satisfying a formula

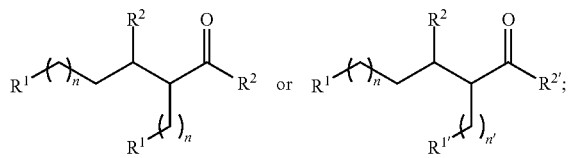

wherein each $R^1$, $R^{1'}$, $R^2$, and $R^{2'}$ independently is selected from hydrogen or aliphatic; each of n and n' independently is selected from 0 to 50; and each m independently is selected from 1-24. These steps can be repeated to provide a saturated oligomerized carbonyl-containing compound having a formula

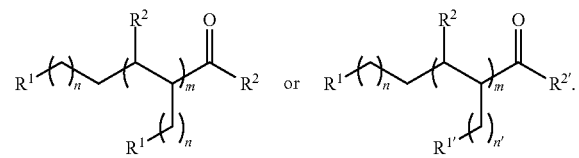

In some embodiments, the method also comprises exposing the saturated oligomerized carbonyl-containing compound to a supported metal catalyst selected from Pd/C, Pd/Al$_2$O$_3$, CuO/Al$_2$O$_3$, Ru/C, or Ni/SiO$_2$—Al$_2$O$_3$; $H_2$; a styrene-divinylbenzene polymer acid, a sulfonated tetrafluoroethylene-based fluoropolymer-copolymer; or any combination thereof, at a temperature below 200° C. to form an aliphatic oligomerized compound having a structure satisfying a formula

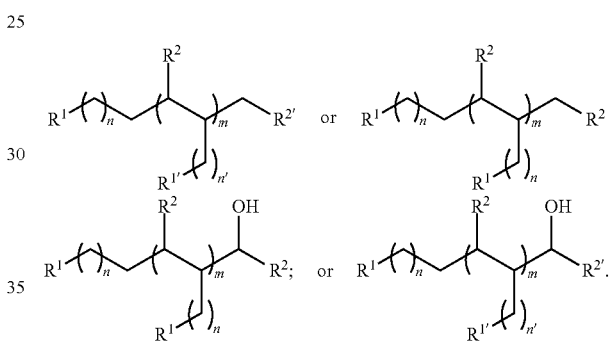

The foregoing and other objects, features, and advantages of the present disclosure will become more apparent from the following detailed description, which proceeds with reference to the accompanying figures.

DETAILED DESCRIPTION

I. Explanation of Terms

Figure 1:
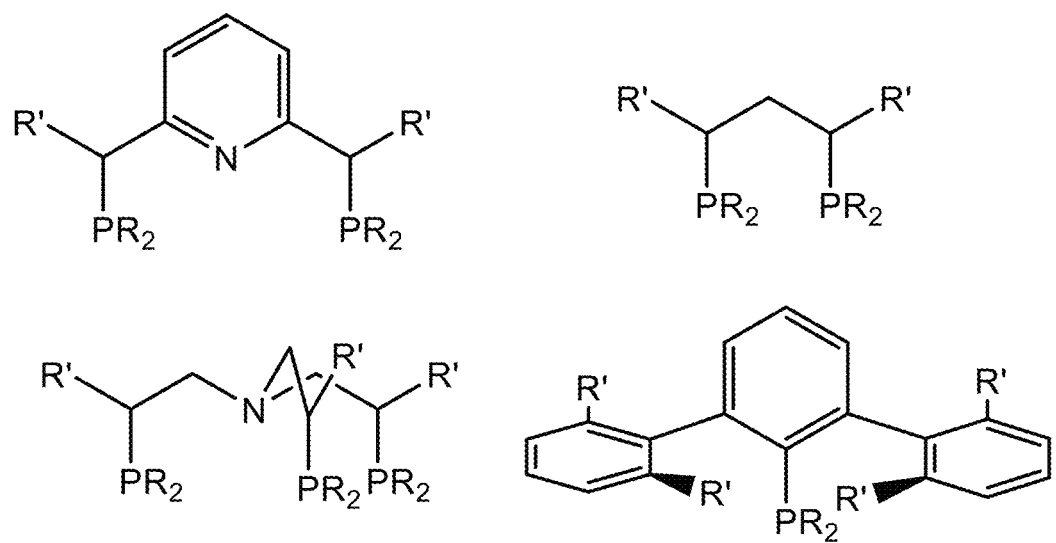
FIG. 1 illustrates exemplary ligands for use in dehydrogenation catalysts described herein.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/ methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided.

Aliphatic: A hydrocarbon, or a radical thereof, having at least one carbon atom to 50 carbon atoms, such as one to 25 carbon atoms, or one to ten carbon atoms, and which includes alkanes (or alkyl), alkenes (or alkenyl), alkynes (or alkynyl), including cyclic versions thereof, and further including straight- and branched-chain arrangements, and all stereo and position isomers as well.

Alkyl: A saturated monovalent hydrocarbon having at least one carbon atom to 50 carbon atoms, such as one to 25 carbon atoms, or one to ten carbon atoms, wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkenyl: An unsaturated monovalent hydrocarbon having at least two carbon atoms to 50 carbon atoms, such as two to 25 carbon atoms, or two to ten carbon atoms, and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cylcoalkenyl), cis, or trans (e.g., E or Z).

Alkynyl: An unsaturated monovalent hydrocarbon having at least two carbon atoms to 50 carbon atoms, such as two to 25 carbon atoms, or two to ten carbon atoms and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Aryl: An aromatic carbocyclic group comprising at least five carbon atoms to 15 carbon atoms, such as five to ten carbon atoms, having a single ring or multiple condensed rings, which condensed rings can or may not be aromatic provided that the point of attachment is through an atom of the aromatic carbocyclic group.

Carbonyl: —C(O)—.

Oligomerized: This term refers to a feature of the products disclosed herein whereby the products produced using the disclosed methods are homologated by one or more carbons relative to the compound (or compounds) from which the products are produced. That is, the products are oligomerized because they have a longer carbon chain than the compound (or compounds) from which they are made. In some embodiments, an oligomerized product can have one or more carbon atoms than the starting compound from which it is made, such as 2-100 more carbon atoms, or 2-80 more carbon atoms, or 2-50 more carbon atoms than the starting compound from which it is made.

A person of ordinary skill in the art would recognize that the definitions provided above are not intended to include impermissible substitution patterns (e.g., methyl substituted with 5 different groups, and the like). Such impermissible substitution patterns are easily recognized by a person of ordinary skill in the art. In some embodiments, dehydrogenation catalyst structures and/or formulas are provided herein that can have an overall complex charge that is neutralized with a suitable counterion. In particular disclosed embodiments, the dehydrogenation catalyst can have an overall positive charge and can further be associated with a suitable counterion (e.g., $^-BAr_4$). Any functional group disclosed herein and/or defined above can be substituted or unsubstituted, unless otherwise indicated herein.

II. Introduction

The use of alcohols for growing longer carbon-based chains has been investigated since the beginning of the $20^{th}$ century with one of the first conversions involving transforming butanol to 2-ethyl-1-hexanol using a strong base and metal oxides at high temperatures and pressures. Despite over a hundred years of subsequent development, the reaction still requires precious metal catalysts in combination with metal oxides or zeolites, as well as high temperatures (e.g., temperatures above 200° C., such as 200° C. to 400° C.) and pressures (e.g., 1000-2000 psi). Also, conventional methods typically only allow for a single coupling reaction, which only doubles the carbon chain length, without the ability to gradually grow the carbon chain, such as by two or more carbon atoms at a time. Some have attempted to vary the carbon chain length by performing the reaction with mixtures of methanol, ethanol and propanol to make carbon chains having up to 5 carbon atoms; however, paraffinic chain lengths of over five carbon atoms that are useful for diesel and aircraft drop-in replacement have not been prepared using such routes.

Some methods have been developed that use alcohols, such as ethanol, to produce carbonyl-containing compounds. In particular, ethanol activation at catalytic surfaces has been studied and two pathways have been determined. In particular, EtOH binds through the oxygen to the surface followed by $C_\beta$—H and O—H bond cleavage resulting in bound ethoxide and hydride. The subsequent step is the rate limiting transformation and either (1) C—O bond cleavage occurs to release ethane, hydroxide, and hydride at the surface; or (2) the $C_\alpha$—H abstraction occurs, releasing acetaldehyde and surface hydride that can either combine to release $H_2$ or a transfer hydrogenation can occur, typically with ethene to give ethane, and thus regenerate the active catalyst. Both products are usually observed in this reaction and precious metal catalysts are required. Furthermore, high temperatures are required, such as temperatures usually above 250° C. The cleavage of C—O bonds is thermally sensitive. The present inventors have determined that methods for forming carbon-chain based fuels utilizing low temperature reaction conditions (e.g., below 200° C., such as 60° C. to 200° C. or lower, or 80° C. to 140° C. or lower) can be used to circumvent this undesired pathway.

Accordingly, disclosed herein are embodiments of a more efficient method for producing fuel by oligomerizing short chain alcohols. While there have been attempts in the art to use an oligomerization approach, these attempts utilized undesirable starting materials (i.e., a trimerization product, 1-hexene, which is not an alcohol), and undesirable catalysts (i.e., pyrophoric zirconium, which is not compatible with volatile alcohols). This prior method further requires a dehydration step that is performed at >300° C., which results in loss of water and valuable hydrogen atoms. Instead of utilizing these hydrogen atoms, conventional methods require using a pure hydrogen gas stream at 50 psi. In contrast, presently disclosed exemplary embodiments retain the $H_2$ released from alcohol dehydrogenation and reincorporate these hydrogen atoms back into reaction products. These embodiments provide a self-contained system that produces valuable fuels at low temperatures, using low cost reagents, and reduce or eliminate the need to use an external hydrogen source.

III. Methods of Making Fuels

Disclosed herein are embodiments of a method for making fuels from alcohols. The disclosed methods are cost efficient and do not require expensive or toxic reagents. The disclosed methods also provide an atom economical approach to making fuels from alcohols by reusing hydrogen atoms (e.g., $H_2$ gas) obtained from catalytic dehydrogenation of readily available alcohols. Some embodiments can be used to produce compounds having aliphatic chains that can be branched or un-branched. In some embodiments, the aliphatic chains can comprise 4 carbon atoms up to 50 carbons atoms, such as 4 carbon atoms to 40 carbon atoms, or 10 carbon atoms to 30 carbon atoms, or 15 carbon atoms to 25 carbon atoms. Particular disclosed embodiments can be used to produce products having aliphatic chains comprising from 10 to 16 carbon atoms. Compounds made using some disclosed exemplary embodiments have a structure satisfying Formula I or Formula II, which are illustrated below.

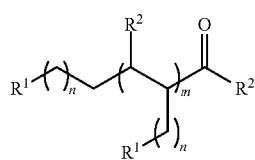

Formula I

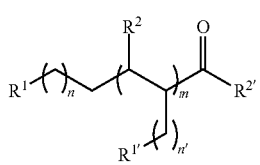

Formula II

With reference to Formulas I and II, each of $R^1$, $R^{1'}$, $R^2$, and $R^{2'}$ independently can be selected from hydrogen or aliphatic; each n and n' independently can be an integer ranging from 0 to 50; and m can be an integer ranging from 1 to 24. In particular disclosed embodiments, each of $R^1$, $R^{1'}$, $R^2$, and $R^{2'}$ independently can be selected from hydrogen or alkyl, such as $C_1$ to $C_{25}$ alkyl (e.g., methyl, ethyl, propyl, butyl, pentyl, hexyl, hepyl, octyl, nonyl, decyl, and the like); each n and n' independently can be an integer ranging from 0 to 25; and m can be an integer ranging from 1 to 8.

In yet additional embodiments, the method can be used to form compounds wherein the carbonyl groups of Formulas I and II are reduced to produce aliphatic compounds, such as branched or unbranched alkanes, or alcohol compounds. In some embodiments, the aliphatic compounds have structures satisfying Formula III or IV below and the alcohol compounds have structures satisfying Formula V or VI. In yet additional embodiments, the method can be used to form acetal-containing products, such as products having structures satisfying Formulas VII or VIII.

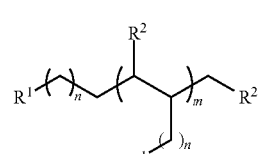

Formula III

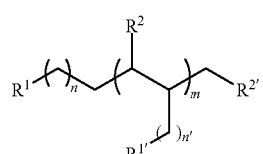

Formula IV

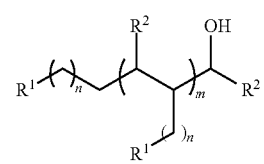

Formula V

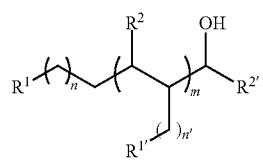

Formula VI

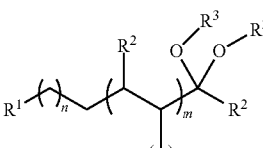

Formula VII

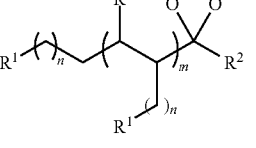

Formula VIII

With reference to Formulas III-VIII, each $R^1$, $R^{1'}$, $R^2$, and $R^{2'}$ independently can be selected from hydrogen or aliphatic; each of n and n' independently can be selected from an integer ranging from 0 to 50; and each m independently is selected from an integer ranging from 1 to 24. With reference to Formulas VII and VIII, each $R^3$ independently can be aliphatic or aryl, with particular embodiments being alkyl (e.g., methyl, ethyl, propyl, butyl, and the like).

In some embodiments, the method can comprise converting an alcohol or mixture of alcohols to a carbonyl-containing compound, which also produces hydrogen gas as a by-product. The method can further comprise converting the carbonyl-containing compound to a condensation product by condensing two of the carbonyl-containing compounds together to form the condensation product, which comprises an α,β-unsaturated carbonyl moiety. The condensation product can then be converted via a reduction step to an oligomerized carbonyl-containing compound by exposing the condensation product to the hydrogen gas by-product produced by converting the starting alcohol(s) to a carbonyl-containing compound. This step reduces the double bond of the α,β-unsaturated carbonyl moiety to a single bond. In some embodiments, this sequence of condensation and reduction steps can be repeated any number of times to produce an oligomerized carbonyl-containing compound having a desired number of carbon atoms in the growing chain. In some embodiments, the method comprises repeating the condensation step and the reduction step to extend the carbon chain of the oligomerized carbonyl-containing compound. In some embodiments, the disclosed method further comprises exposing the oligomerized carbonyl-containing compound to a metal catalyst on a support material in combination with a solid acid catalyst to form an alkane compound.

Embodiments of the disclosed method steps are illustrated below in Scheme 1. In some embodiments, the method can use a single starting alcohol species. In yet other embodiments, the method of Scheme 1 can use a combination of alcohol starting materials, such as alcohol 100 and methanol ($CH_3OH$).

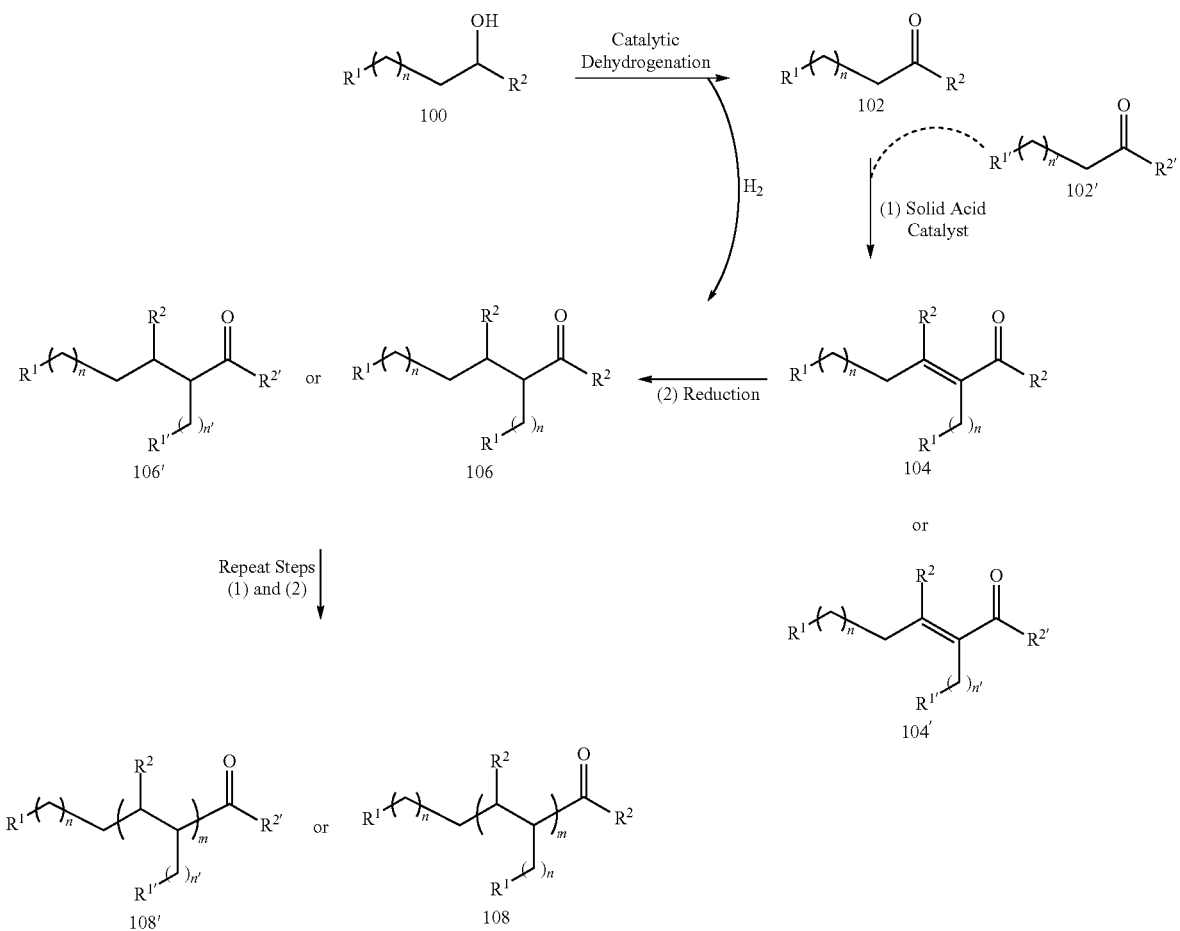

With reference to Scheme 1, alcohol 100 can be catalytically dehydrogenated to form carbonyl-containing compound 102 using a catalytic dehydrogenation reagent, such as a dehydrogenation catalyst disclosed below. The carbonyl-containing compound 102 can then undergo a condensation-based oligomerization reaction with another identical carbonyl-containing compound 102, or a structurally different carbonyl-containing compound 102' (wherein at least one of $R^{1'}$, $R^{2'}$, or n' is different from $R^1$, $R^2$, or n of compound 102) to form condensation products 104 or 104'. Condensation products 104 or 104' can then be reduced to oligomerized carbonyl-containing products 106 or 106'. By repeating the condensation-based oligomerization reaction and the reduction reaction, as many times as may be desired, products 106 and 106' can be oligomerized further to extend the carbon chain and produce products 108 or 108' as illustrated in Scheme 1. In particular disclosed embodiments, a carbonyl-containing starting material can be used rather than an alcohol. Such carbonyl-containing starting materials can be obtained as enzyme-catalyzed degradation products and utilized in the method disclosed herein.

The catalytic dehydrogenation step illustrated in Scheme 1 also can be referred to herein as an acceptor-less alcohol dehydrogenation step as it does not require an external hydrogen acceptor (e.g., another chemical moiety, such as a ketone, olefin, or halocarbon, to which the hydrogen is transferred). In some embodiments, the acceptor-less alcohol dehydrogenation step can be used to produce one carbonyl-containing compound or it can be used with a mixture of alcohols to produce a mixture of corresponding carbonyl-containing compounds. The carbonyl-containing compounds (or mixture of carbonyl-containing compounds) produced from the acceptor-less alcohol dehydrogenation step can then be converted to a condensation product (or mixture of condensation products) using the above-described, condensation-based oligomerization step. As indicated above, the condensation-based oligomerization step combines two of the carbonyl-containing compounds, which can be the same or different (e.g., compounds 102 or 102' as illustrated in Scheme 1) to form an oligomerized carbonyl-containing compound. In some embodiments, this step can be an aldol reaction step (such as when two aldehyde compounds are combined, which can be the same or different). The condensation product can be reacted with hydrogen gas, such as the hydrogen gas by-product produced from dehydrogenation of the alcohol or mixture of alcohols, to form an oligomerized carbonyl-containing compound that is then capable of again being extended using another carbonyl-containing compound. The chain can be continuously extended using a combination of this condensation-based oligomerization reaction and the reduction reaction.

Exemplary method embodiments are illustrated below in Schemes 2 and 3.

Scheme 2

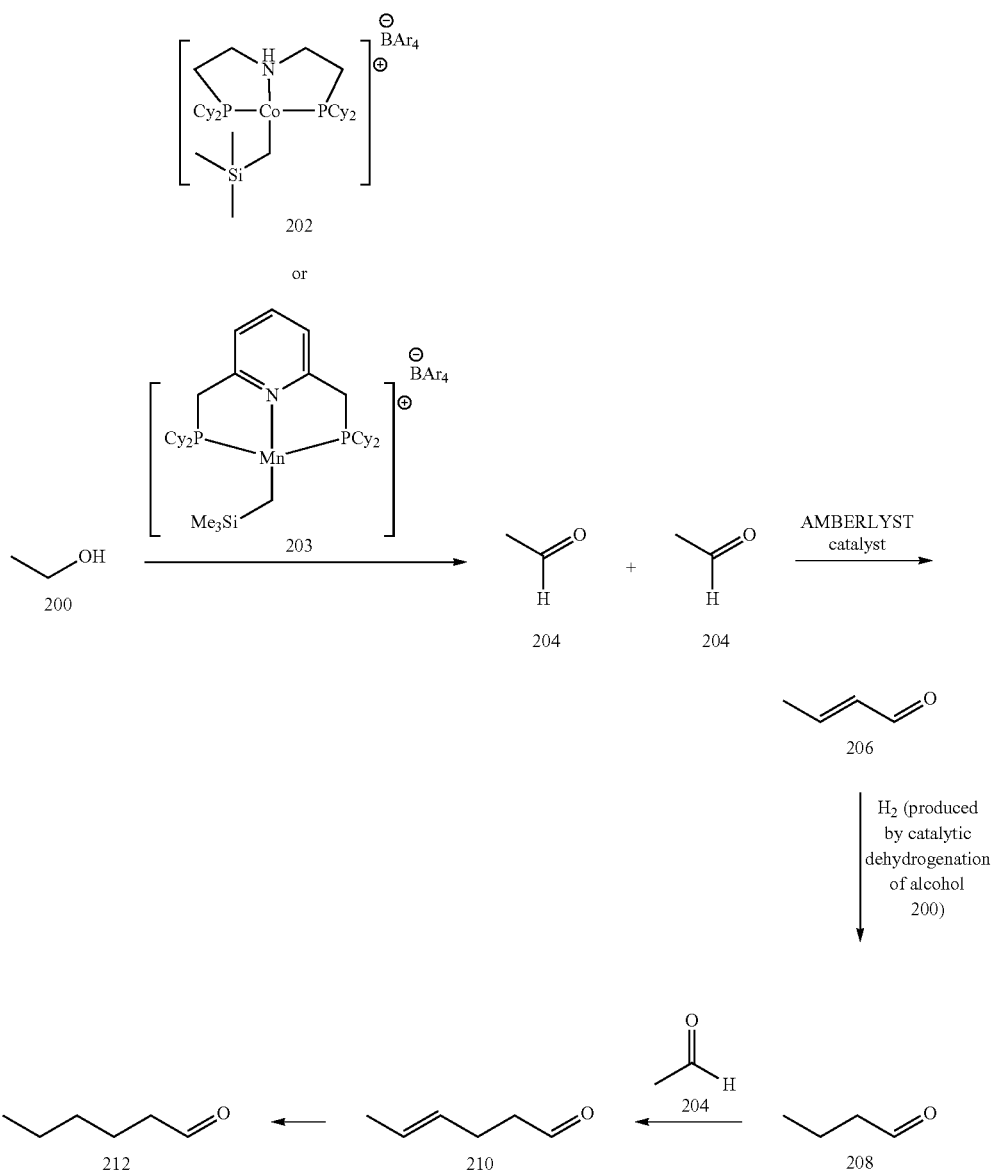

Scheme 3

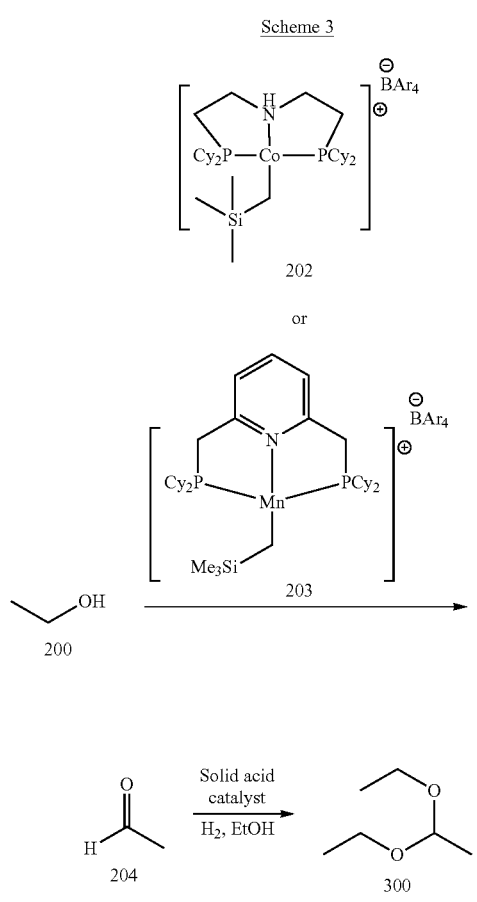

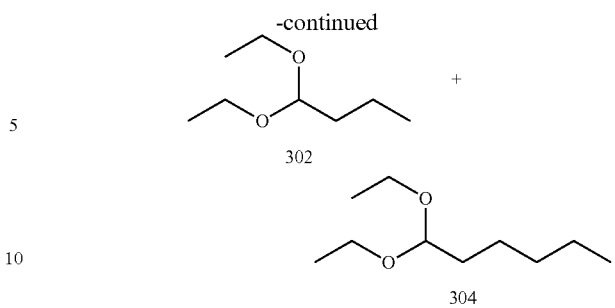

With reference to Schemes 2 and 3, other dehydrogenation catalysts comprising a transition metal supported by heteroatom-containing coordinating ligands can be used, including, but not limited to a catalyst having a structure satisfying a formula provided by Table 1 (included herein). Also, and as illustrated in Scheme 3, carbon chain-extended acetal products (e.g., 302 and 304) can be formed by using alcohol solvents (e.g., methanol, ethanol, propanol, or the like). In some embodiments, the alcohol solvent can be added at any point during the reaction and in some embodiments can be added with the starting carbonyl-containing compound or separately. In particular disclosed embodiments, the alcohol solvent can be added to convert a carbonyl-containing compound comprising an α,β-unsaturated carbonyl group to an acetal-containing compound. In yet additional embodiments, the alcohol solvent can be added to convert a saturated carbonyl-containing compound to a saturated acetal-containing compound.

In some embodiments, the method can further comprise reducing the oligomerized carbonyl-containing compounds to aliphatic compounds and/or alcohol-containing compounds, such as is illustrated in Schemes 4 and 5, respectively.

Scheme 4

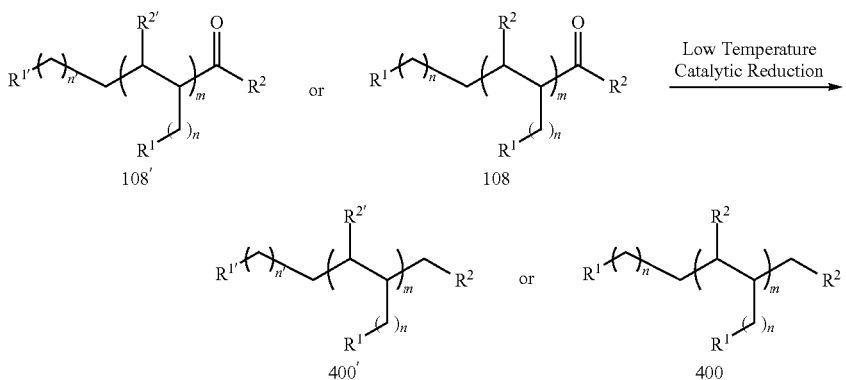

Scheme 5

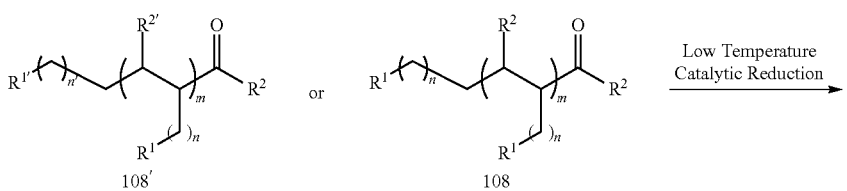

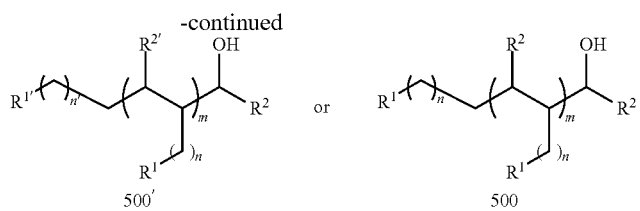

500'  or  500

With reference to Scheme 4, oligomerized carbonyl-containing compounds 108 and 108' can be converted to aliphatic compounds 400 and 400', respectively, using a low temperature catalytic reduction step. In some embodiments, the low temperature catalytic reduction step comprises exposing the oligomerized carbonyl-containing compound to a metal catalyst, a support component, hydrogen gas, and a solid acid catalyst. Similar reagents can be used to convert the oligomerized carbonyl-containing compounds 108 and 108' to alcohol containing compounds 500 and 500', respectively (Scheme 5).

The metal catalyst can be selected from a metal belonging to Group 10 of the periodic table, such as Ni, Pd, or Pt; a metal selected from Group 11 of the periodic table, such as Cu, Ag, or Au; or a metal selected from Group 8 of the periodic table, such as Fe or Ru. In particular disclosed embodiments, the metal catalyst is a Pd catalyst, a CuO catalyst, a Ru catalyst, or a Ni catalyst. In some embodiments, the Pd catalyst can further comprise a solid support, such as a carbon-based support (e.g., activated carbon, carbon, carbon black, and the like), an oxide-based support (e.g., $Al_2O_3$, $SiO_2$, $SiO_2$—$Al_2O_3$, and the like), or a combination thereof. Exemplary metal catalysts used in some embodiments include, but are not limited to, Pd/C, Pd/$Al_2O_3$, CuO/$Al_2O_3$, Ru/C, and Ni/$SiO_2$—$Al_2O_3$.

The solid acid can be selected from a zeolite-based solid acid, a polymer-based solid acid, a carbon-based solid acid, a hydroxyapatite-based solid acid, a zirconia-based solid acid, or a silica-based solid acid. In particular disclosed embodiments, the solid acid is a polymer-based acid, such as a styrene-divinylbenzene polymer acid, or a sulfonated tetrafluoroethylene-based fluoropolymer-copolymer. In some embodiments, the solid acid catalyst can be a sulfonated tetrafluoroethylene-based fluoropolymer-copolymer (e.g., a NAFION® catalyst), a styrene-divinylbenzene polymer acid (e.g., AMBERLYST® catalyst, such as an AMBERLYST® 15 ion exchange resin, an AMBERLYST® 36 ion exchange resin, or the like), a zeolite-based polymer (e.g., H-ZSM-5 or the like), or a combination thereof.

In some embodiments, the low temperature catalytic reduction step can be carried out at temperatures below 200° C., such as temperatures ranging from 80° C. to 150° C., or 80° C. to 100° C., or 80° C. to 90° C. In some embodiments, the low temperature catalytic reduction step can be carried out at temperatures at or below 120° C. In embodiments using a zeolite catalyst, the low temperature catalytic reduction step can be carried out at temperatures above 120° C. and ranging to a temperature that does not degrade or deactivate the zeolite catalyst. A solvent can also be used in the methods described herein. Exemplary solvents include water, non-aqueous solvents (e.g., tetrahydrofuran, cyclohexane, toluene, ethanol, or the like), or combinations thereof.

An exemplary embodiment of the method shown in Scheme 4 is provided below in Scheme 6.

Scheme 6

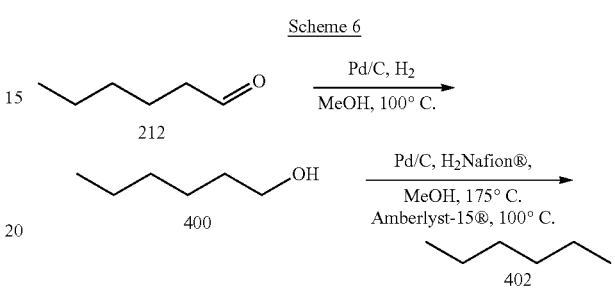

An exemplary embodiment of the method shown in Scheme 5 is illustrated below in Scheme 7.

Scheme 7

As indicated above, the method embodiments disclosed herein can concern using catalysts that are cost-efficient and therefore suitable for use in industrial settings. The catalysts also can function at low temperatures, which also makes them suitable for industrial-scale methods. In some embodiments, the dehydrogenation catalyst used in the acceptor-less alcohol dehydrogenation reaction to convert the alcohol feedstock into its corresponding carbonyl-containing compound can also be used to catalyze the condensation-based oligomerization reaction wherein the condensation product is hydrogenated to produce a corresponding saturated, oligomerized, carbonyl-containing compound. In some embodiments, the dehydrogenation catalyst can be selected from metal-containing catalysts, with particular embodiments being non-precious metal-based catalysts. In some embodiments, the dehydrogenation catalysts comprise a transition metal, with particular embodiments being selected from cobalt, manganese, or ruthenium; and a hydride source. In some embodiments, the dehydrogenation catalysts comprise a metal mono-hydride or a metal di-hydride species and further comprise ligands that stabilize the metal mono-hydride or metal di-hydride species. The supporting ligand typically is a neutral donor that stabilizes the metal center and allow for hydrides to bind. Such ligands can be selected from, but are not limited to the ligands illustrated in FIG. 1 and provided by Table 1, below.

In some embodiments, manganese hydrides are used as the dehydrogenation catalyst. Such dehydrogenation catalysts can reversibly cleave $H_2$ heterolytically, which is a reactivity that is useful for dehydrogenation as it demonstrates the ability of manganese to accept hydrides and protons and release $H_2$ and potentially perform transfer hydrogenation. Control over the electronics at the metal center can be used to increase or decrease the electrophilicity at the manganese metal. Also, steric changes around the metal can be obtained by incorporating bulky groups. And labile phosphine ligands can be used to provide additional metal reaction sites. Similarly, bis(diphosphines) with iron can be released upon reduction to $Fe^{+1}$ and then rebind on oxidation to stabilize the dehydrogenation catalyst. Accordingly, in some embodiments, chromium- and iron-containing dehydrogenation catalysts can be used. In yet other embodiments, ruthenium dehydrogenation catalysts, such as $[RuH_2(N_2)(PPh_3)_3]$, can be modified using different ligands to reduce the steric hindrance about the metal center and thereby lower the kinetic barrier associated with the acceptor-less alcohol dehydrogenation reaction and yield a better dehydrogenation catalyst. In some embodiments, the catalyst can be provided in an amount ranging from 0.05 wt % to 20 wt %, such as 0.05 wt % to 15 wt %, or 0.05 wt % to 10 wt %, or 0.1 wt % to 5 wt %. The dehydrogenation catalysts can be made using synthetic techniques typically employed to facilitate ligand-metal complexation, such as by reacting a metal precursor (e.g., a metal ion, a metal atom, or a metal-containing compound) with a desired ligand in a suitable solvent and then isolating the dehydrogenation catalyst.

In particular disclosed embodiments, the dehydrogenation catalyst is selected from catalysts having structures satisfying the complexes illustrated below in Table 1:

TABLE 1

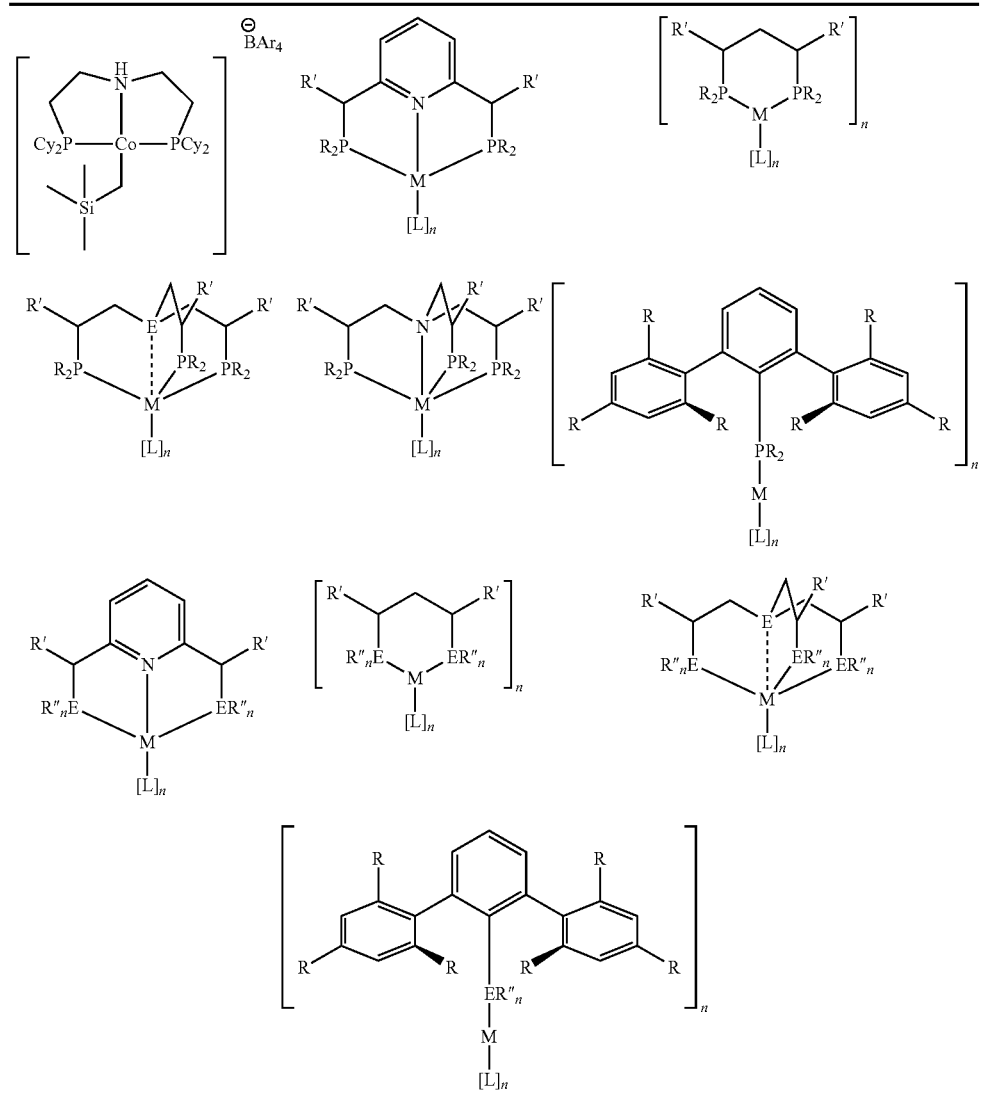

wherein each of L, R, and R' independently can be selected from alkyl, aryl, H, or ER''$_n$ (wherein n is 1, 2, 3, or 4, E is selected from B, C, O, N, P, S, or Si, and R" is selected from hydrogen, alkyl, or aryl); E is selected from B, C, O, N, P, S, or Si; R" is selected from hydrogen, alkyl, or aryl, each n is an integer selected from 0 to 4, and M is selected from Mn, Fe, Co, or Cr.

Suitable alcohols that can be used in the disclosed methods include, but are not limited to aliphatic alcohols, such as alkyl alcohols. In some embodiments, the alcohols can be branched alcohols, or straight chain alcohols. In some embodiments, the alcohols comprise at least one hydroxyl group and in some embodiments can comprise two or more hydroxyl groups. The at least one hydroxyl group can be a terminal hydroxyl group (e.g., —CH$_2$OH or —CRH—OH) or it can be positioned within the aliphatic chain of the alcohol (e.g., —HC(OH)—). Exemplary alcohols include, but are not limited to methanol, ethanol, propanol, isopropanol, butanol, isobutanol, pentanol (and isomers thereof), hexanol (and isomers thereof), and the like.

IV. Examples

Example 1

Figure 2:
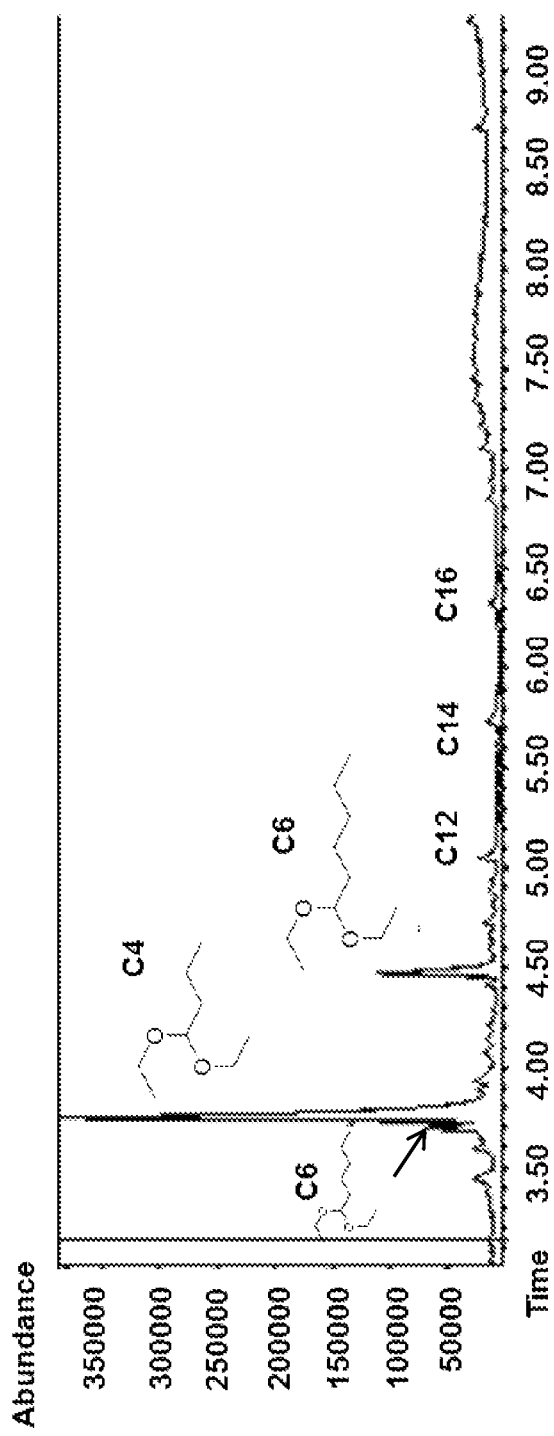
FIG. 2 is a gas chromatogram illustrating results obtained from disclosed method embodiments.

In one example, acetaldehyde (which can be produced by exposing ethanol to a stoichiometric or catalytic amount of a dehydrogenatation catalyst disclosed herein) and crotonaldehyde (which can be produced by exposing (E)-but-2-en-1-ol to a stoichiometric or catalytic amount of a dehydrogenation catalyst disclosed herein) were combined to form a chain-extended product under very mild conditions using a solid acid catalyst. With ethanol solutions of acetaldehyde, a solid acid catalyst and 50 psi H$_2$ with Pd/C as the hydrogenation catalyst were sealed in a reaction vessel and heated at 100° C. for 120 minutes. The results indicated complete conversion of acetaldehyde and the formation of molecules with between 4 and 16 carbons as the main products as evidenced by the GC-MS of the crude reaction mixtures (FIG. 2). Further heating for a total of 5 hours provided heaver molecules with at least 20 carbon atoms.

Example 2

Figure 3:
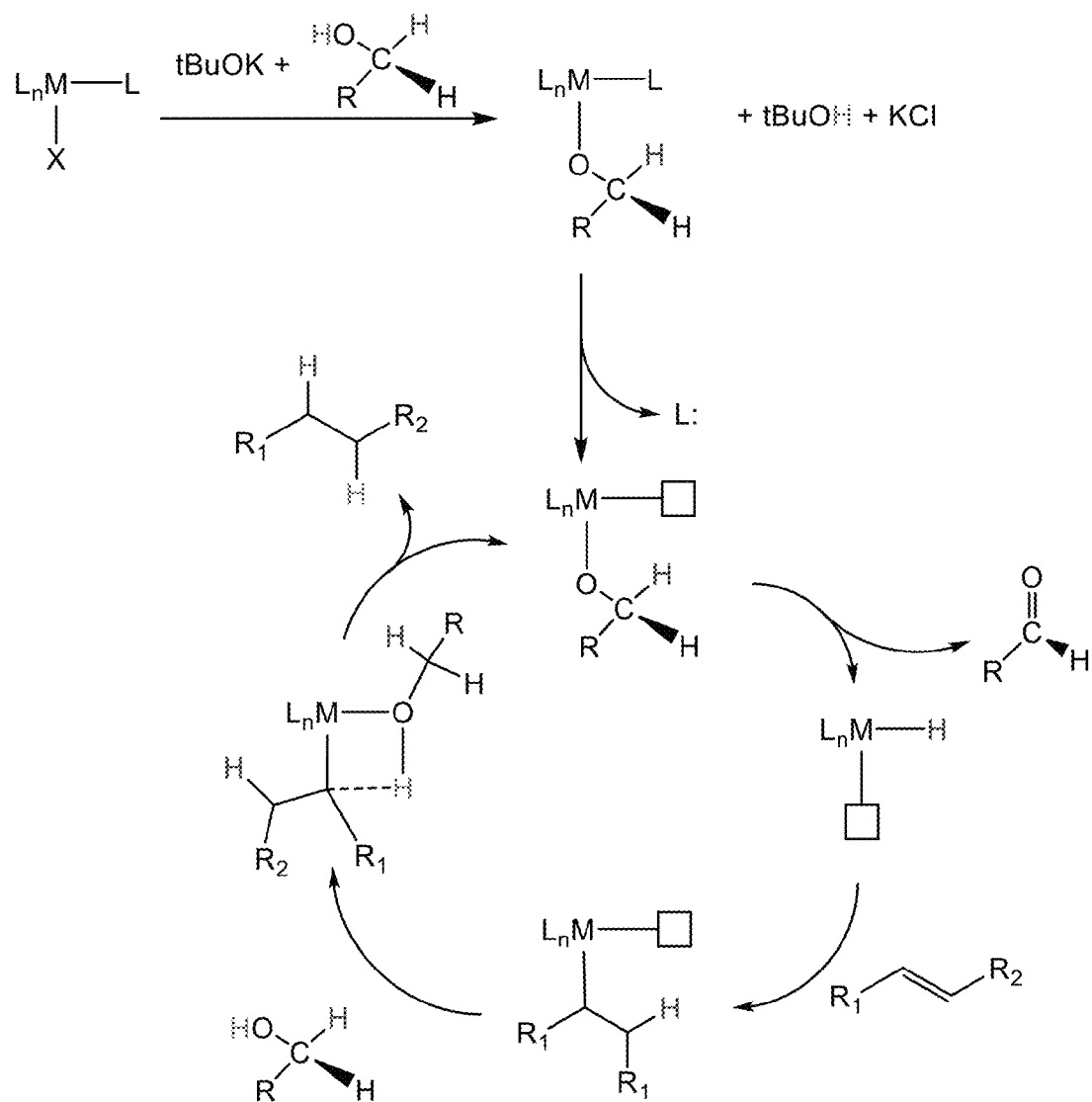
FIG. 3 illustrates an exemplary reaction mechanism showing various exemplary steps and compounds that can be formed using disclosed method embodiments.

In some embodiments, all compound intermediates illustrated in FIG. 3 can be synthesized to determine the stability of the compounds with different metal/ligand combinations and then interconverted stepwise to understand the transformation, prove its viability, determine the reaction steps, and turn the process into a catalytic process.

Example 3

Figure 4:
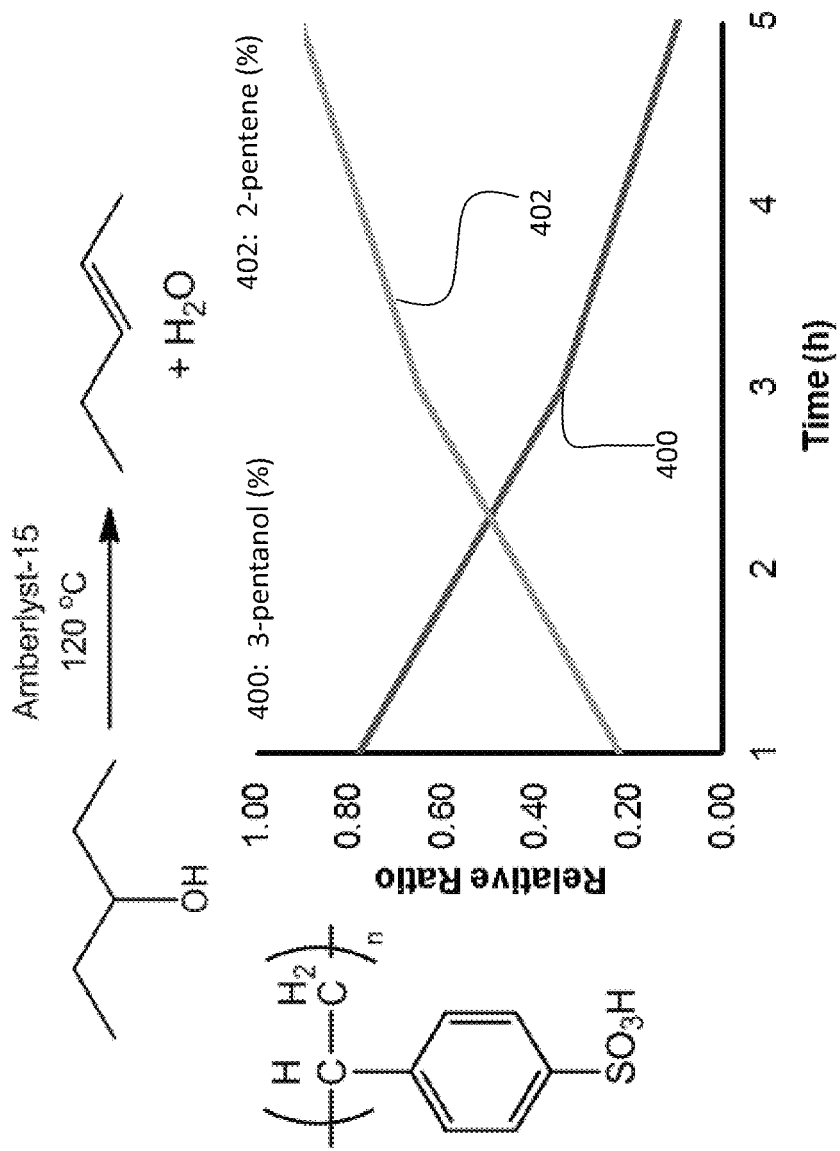
FIG. 4 is graph of relative ratio as a function of time (hours) illustrating reaction progress during the conversion of a reduced carbonyl-containing compound to an aliphatic fuel precursor using an exemplary solid acid catalyst.
Figure 5:
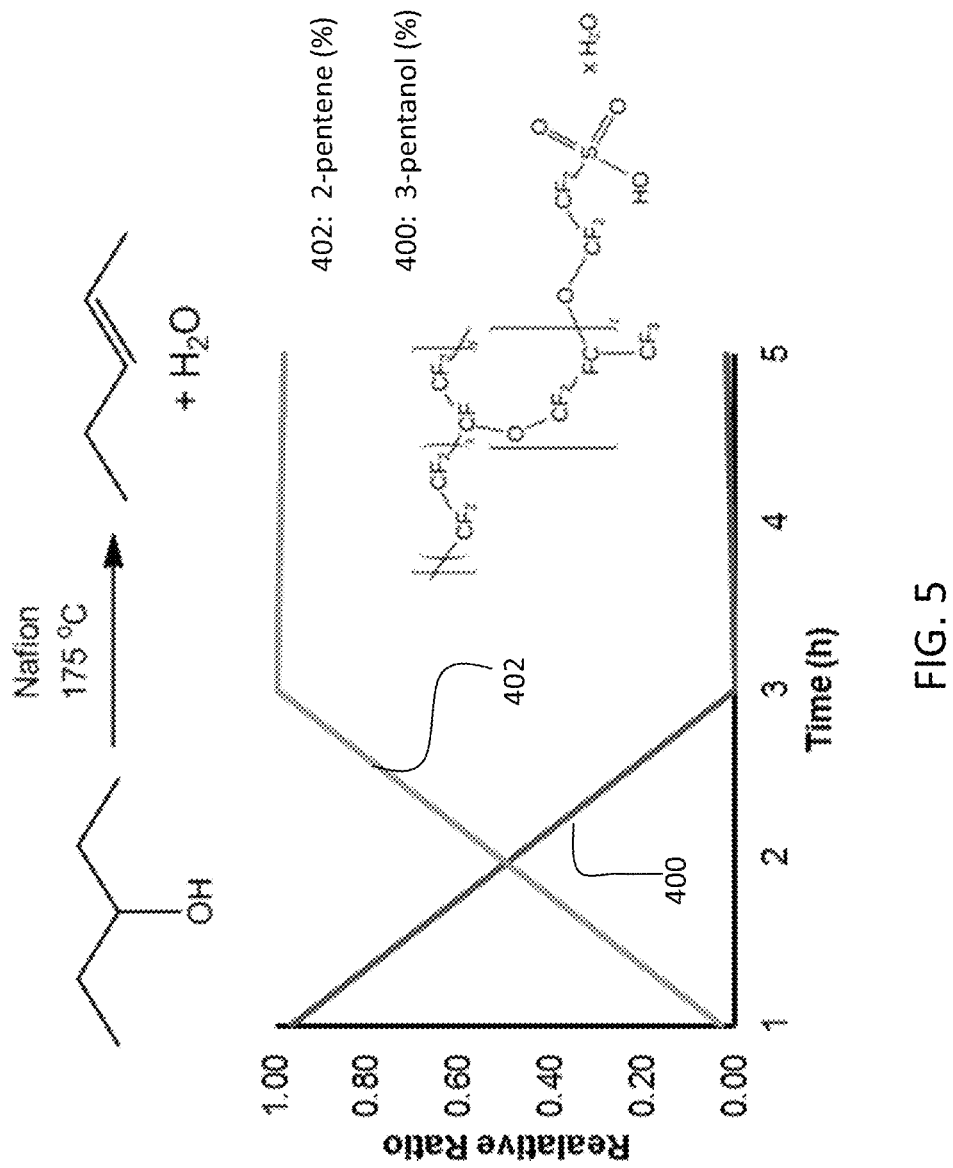
FIG. 5 is graph of relative ratio as a function of time (hours) illustrating reaction progress during the conversion of a reduced carbonyl-containing compound to an aliphatic fuel precursor using another exemplary solid acid catalyst.

In some embodiments, the ability to convert oligomerized carbonyl-containing compounds to aliphatic compounds suitable for use as fuels was established by reducing the oligomerized carbonyl-containing compound to the corresponding alcohol and then converting the resulting alcohol to an alkene-containing compound using a solid acid catalyst disclosed herein (e.g., AMBERLYST-15® ion exchange resin and/or a NAFION® catalyst). FIGS. 4 and 5 provide graphical results of such a conversion. The alkene-containing compound can be further reduced to the corresponding saturated aliphatic compound using an additional solid acid catalyst step. In some embodiments, each of the chemical conversions described in this example can be performed sequentially, or they can be performed in one step.

Example 4

In this example, an acid catalyst (0.1-0.4 g) and a metal catalyst (1-10 mol % metal, relative to acetaldehyde) are added to a stainless steel sample cylinder. A stock solution of acetaldehyde in solvent (2-4 mL of ca. 1 M concentration) is then added to the sample cylinder and sealed. The cylinder is pressurized with H$_2$ (5-60 psig) or dilute H$_2$/Ar (6% H$_2$; 100-300 psig) and heated (60-120° C.) for 2 to 16 hours. The reaction is then diluted with an organic solvent (e.g., ethyl acetate), separated from the catalysts, and analyzed by GCMS. In some embodiments using these parameters, carbon yields of $C_{6+}$ aldehydes can be obtained in yields reaching 40% or higher. In some embodiments, ethanol can be used as the solvent, which can provide $C_{4+}$ acetals in yields reaching 40% or higher.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method, comprising:
exposing an alcohol or a mixture of alcohols to a dehydrogenation catalyst capable of dehydrogenating the alcohol or the mixture of alcohols to produce H$_2$ and a carbonyl-containing compound, or a mixture of carbonyl-containing compounds;
exposing the carbonyl-containing compound or mixture of carbonyl-containing compounds to a solid acid catalyst to produce a condensation product comprising an α,β-unsaturated carbonyl group, wherein the condensation product is converted to a saturated oligomerized carbonyl-containing compound in the presence of H$_2$ produced from dehydrogenating the alcohol or mixture of alcohols;
wherein the dehydrogenation catalyst is selected from

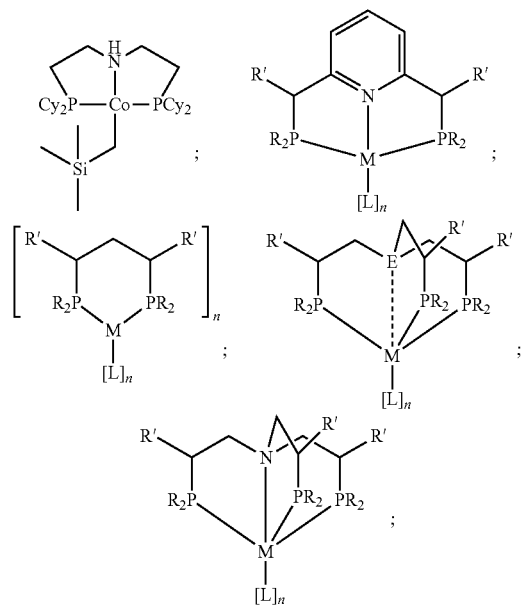

-continued

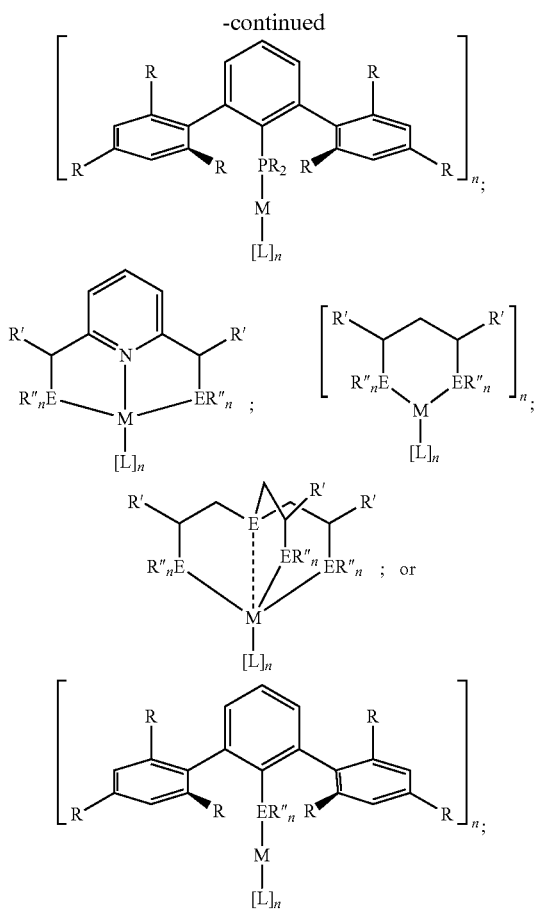

wherein each of L, R, and R' independently can be selected from alkyl, aryl, H, or $ER''_n$ (wherein n is 1, 2, 3, or 4, E is selected from B, C, O, N, P, S, or Si, and R'' is selected from hydrogen, alkyl, or aryl); E is selected from B, C, O, N, P, S, or Si; R'' is selected from hydrogen, alkyl, or aryl, each n is an integer selected from 0 to 4, and M is selected from Mn, Fe, Co, or Cr.

2. The method of claim 1, wherein the method further comprises exposing the saturated oligomerized carbonyl-containing compound to a metal catalyst, a solid acid catalyst, or a combination thereof at a temperature below 200° C. to form an aliphatic compound.

3. The method of claim 1, wherein M is selected from cobalt, manganese, or iron.

4. The method of claim 1, wherein the carbonyl-containing compound has a structure satisfying a formula

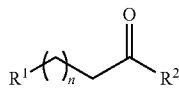

wherein each of $R^1$ and $R^2$ is hydrogen or aliphatic, and n ranges from 0 to 50.

5. The method of claim 1, wherein the condensation product is formed by a condensation reaction between two carbonyl-containing compounds having the same structure and wherein the condensation product has a structure satisfying a formula

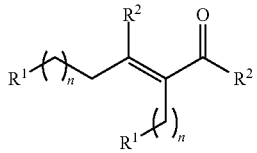

wherein each $R^1$ and $R^2$ is hydrogen or aliphatic, and each n ranges from 0 to 50.

6. The method of claim 1, wherein the condensation product is formed by a condensation reaction between a mixture of carbonyl-containing compounds having different structures and wherein the condensation product has a structure satisfying a formula

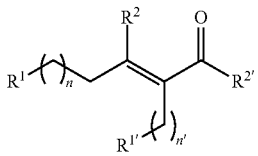

wherein each $R^1$, $R^{1'}$, $R^2$, and $R^{2'}$ independently is selected from hydrogen or aliphatic; and each of n and n' independently is selected from 0 to 50.

7. The method of claim 1, wherein exposing the carbonyl-containing compound or mixture of carbonyl-containing compounds to the solid acid catalyst comprises reacting the carbonyl-containing compound or mixture of carbonyl-containing compounds with a styrene-divinylbenzene polymer acid or a sulfonated tetrafluoroethylene-based fluoropolymer-copolymer.

8. The method of claim 1, wherein the condensation product is converted to the saturated oligomerized carbonyl-containing compound by exposing the condensation product to $H_2$ produced from dehydrogenating the alcohol or mixture of alcohols by transferring $H_2$ from a first reaction vessel wherein the alcohol or mixture of alcohols has been dehydrogenated to a second reaction vessel comprising the condensation product.

9. The method of claim 1, wherein the condensation product is converted to the saturated oligomerized carbonyl-containing compound by adding the solid acid catalyst into a reaction vessel comprising the $H_2$ produced by dehydrogenation of the alcohol or mixture of alcohols and the carbonyl-containing compound or the mixture of carbonyl-containing compounds.

10. The method of claim 1, further comprising repeating the step of exposing the carbonyl-containing compound or mixture of carbonyl-containing compounds to a solid acid catalyst in the presence of $H_2$ to obtain a saturated oligomerized carbonyl-containing compound having a structure satisfying a formula $$R^1\!\!\left(\!\!\begin{array}{c}\end{array}\!\!\right)_{\!n}\!\!\left(\!\!\begin{array}{c}R^2\\ \\R^{1'}\!\!\left(\!\!\begin{array}{c}\end{array}\!\!\right)_{\!n'}\end{array}\!\!\right)_{\!m}\!\!\overset{O}{\underset{}{\|}}\!R^{2'} \quad \text{or} \quad R^1\!\!\left(\!\!\begin{array}{c}\end{array}\!\!\right)_{\!n}\!\!\left(\!\!\begin{array}{c}R^2\\ \\R^{1'}\!\!\left(\!\!\begin{array}{c}\end{array}\!\!\right)_{\!n}\end{array}\!\!\right)_{\!m}\!\!\overset{O}{\underset{}{\|}}\!R^2;$$

wherein each $R^1$, $R^{1'}$, $R^2$, and $R^{2'}$ independently is selected from hydrogen or aliphatic; each of n and n' independently is selected from 0 to 50; and each m independently is selected from 1-24.

11. The method of claim 1, further comprising adding an alcohol solvent to convert the condensation product comprising an α,β-unsaturated carbonyl group to an acetal-containing product.

12. The method of claim 1, further comprising adding an alcohol solvent to convert the saturated oligomerized carbonyl-containing compound to a saturated oligomerized acetal-containing compound.

13. The method of claim 10, further comprising exposing the saturated oligomerized carbonyl-containing compound to a supported metal catalyst selected from Pd/C, Pd/Al$_2$O$_3$, CuO/Al$_2$O$_3$, Ru/C, and Ni/SiO$_2$—Al$_2$O$_3$; H$_2$; a styrene-divinylbenzene polymer acid, a sulfonated tetrafluoroethylene-based fluoropolymer-copolymer; or any combination thereof at a temperature below 200° C. to form an aliphatic oligomerized compound having a structure satisfying a formula

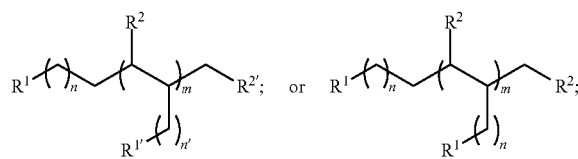

or an alcohol-containing oligomerized compound having a structure satisfying a formula

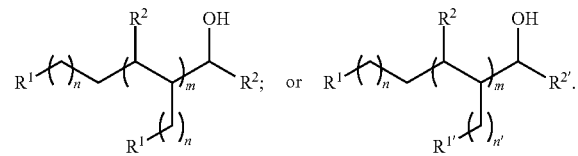

14. A method, comprising:
exposing an alcohol or mixture of alcohols to a dehydrogenation catalyst capable of dehydrogenating the alcohol or the mixture of alcohols to produce a carbonyl-containing compound having a structure satisfying a formula

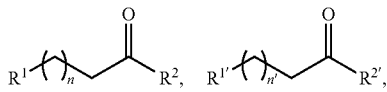

or a mixture thereof, and H$_2$;
exposing the carbonyl-containing compound or mixture thereof to a styrene-divinylbenzene polymer acid or a sulfonated tetrafluoroethylene-based fluoropolymer-copolymer to produce an oligomerized condensation product having a structure satisfying a formula

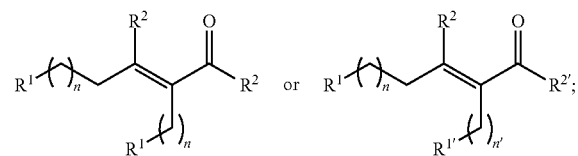

wherein the oligomerized condensation product is converted to a saturated oligomerized carbonyl-containing compound in the presence of H$_2$ produced from the dehydrogenation of the alcohol or mixture of alcohols, wherein the saturated oligomerized carbonyl-containing compound has a structure satisfying a formula

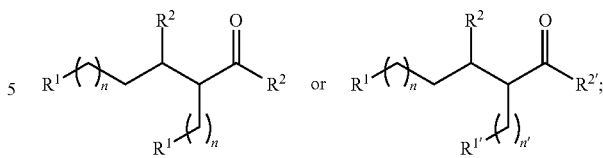

wherein each R$^1$, R$^{1'}$, R$^2$, and R$^{2'}$ independently is selected from hydrogen or aliphatic; each of n and n' independently is selected from 0 to 50; and each m independently is selected from 1-24;

wherein the dehydrogenation catalyst is selected from

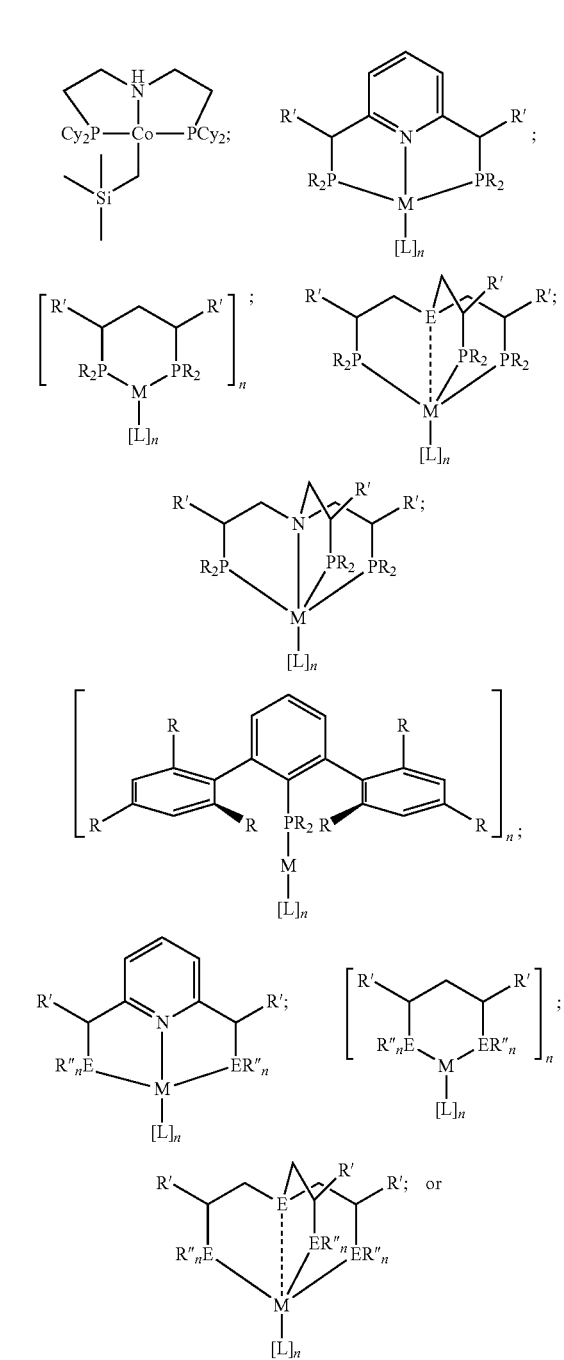

-continued

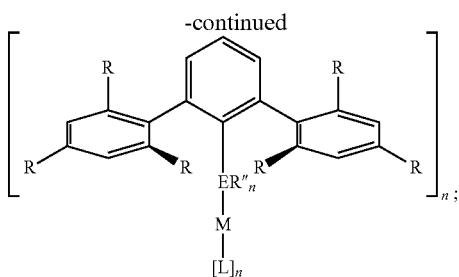

wherein each of L, R, and R' independently can be selected from alkyl, aryl, H, or ER"$_n$ (wherein n is 1, 2, 3, or 4, E is selected from B, C, O, N, P, S, or Si, and R" is selected from hydrogen, alkyl, or aryl); E is selected from B, C, O, N, P, S, or Si; R" is selected from hydrogen, alkyl, or aryl, each n is an integer selected from 0 to 4, and M is selected from Mn, Fe, Co, or Cr.

15. The method of claim 14, further comprising repeating the method to obtain a saturated oligomerized carbonyl-containing compound having a structure satisfying a formula

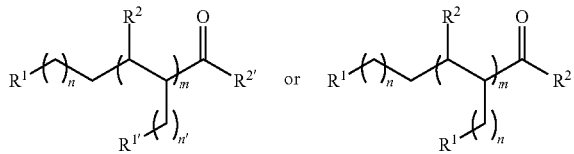

wherein each R$^1$, R$^{1'}$, R$^2$, and R$^{2'}$ independently is selected from hydrogen or aliphatic; each of n and n' independently is selected from 0 to 50; and each m independently is selected from 1-24.

16. The method of claim 15, further comprising exposing the saturated oligomerized carbonyl-containing compound to a supported metal catalyst selected from Pd/C, Pd/Al$_2$O$_3$, CuO/Al$_2$O$_3$, Ru/C, and Ni/SiO$_2$—Al$_2$O$_3$; H$_2$; a styrene-divinylbenzene polymer acid, a sulfonated tetrafluoroethylene-based fluoropolymer-copolymer; or any combination thereof at a temperature below 200° C. to form an aliphatic oligomerized compound having a structure satisfying a formula

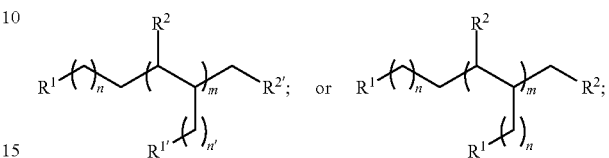

or an alcohol-containing oligomerized compound having a structure satisfying a formula

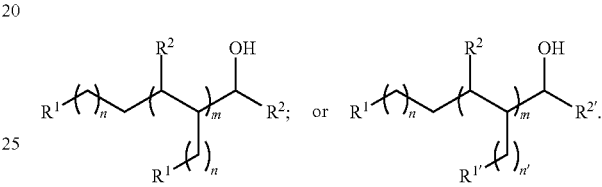

17. The method of claim 14, further comprising adding an alcohol solvent to convert the oligomerized condensation product to an oligomerized acetal-containing compound.

18. The method of claim 14, further comprising adding an alcohol solvent to convert the saturated oligomerized carbonyl-containing compound to a saturated oligomerized acetal-containing compound.

* * * * *